Figure 1:
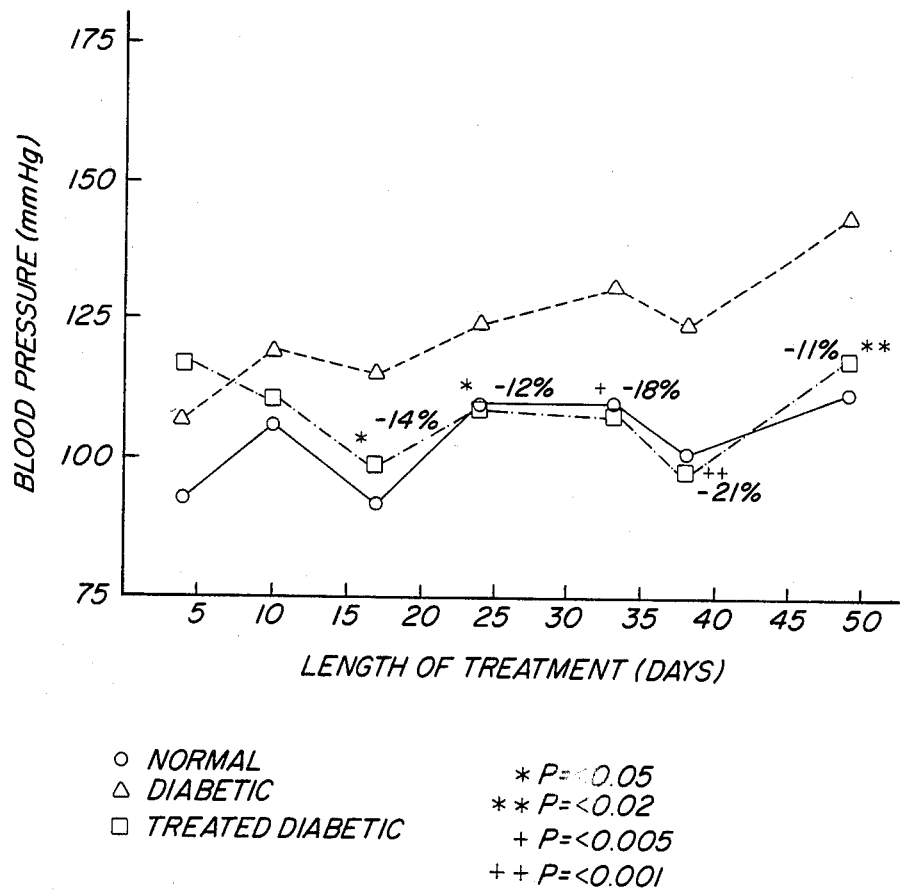

United States Patent [19]

Hartmann

[11] Patent Number: 4,798,821

[45] Date of Patent: Jan. 17, 1989

[54] ANTIHYPERTENSIVE THERAPY FOR DIABETICS

[75] Inventor: John F. Hartmann, Princeton Junction, N.J.

[73] Assignee: Merck & Co., Inc., Rahway, N.J.

[21] Appl. No.: 20,611

[22] Filed: Mar. 2, 1987

[51] Int. Cl.$^4$ .................. A61K 37/02; C07K 7/26
[52] U.S. Cl. .................................. 514/9; 514/10; 514/11; 514/806; 530/311
[58] Field of Search ............... 514/9, 10, 11, 806; 530/311

[56] References Cited

U.S. PATENT DOCUMENTS

| | | | |
|---|---|---|---|
| 4,235,886 | 11/1980 | Freidinger et al. | 574/11 |
| 4,238,481 | 12/1980 | Rink et al. | 514/11 |
| 4,310,518 | 1/1982 | Freidinger et al. | 514/11 |
| 4,358,439 | 11/1982 | Sieber et al. | 530/311 |
| 4,522,813 | 6/1985 | Nutt | 514/11 |
| 4,585,755 | 4/1986 | Morgan et al. | 514/11 |
| 4,663,435 | 5/1987 | Brady | 530/311 |

FOREIGN PATENT DOCUMENTS 0187622 7/1986 European Pat. Off. .
2095261 9/1982 United Kingdom .

OTHER PUBLICATIONS

Vale et al., Metabolism 27, Suppl. 1, pp. 1391–1401 (1978).
Rivier, J. Am. Chem. Soc. 96, 2986 (1974).
Rivier et al, J. Med. Chem. 18, 123 (1975).
Veber et al, Nature, 292, 55 (1981).
Bauer et al, "Peptides 1982", Proceedings of the 17th European Peptide Symposium, pp. 583–588, edited by K. Blaha and P. Malon; Walter de Gruyter, NY (1983).
Bauer et al, Life Science, 31, pp. 1133–1140 (1982).
Pless et al, Scand. J. Gastroenterol 21, pp. 54–64 (Suppl. 119) (1986).
Blech, Biol. Abstr. 67 (5), 30197 (1978).

*Primary Examiner*—Johnnie R. Brown
*Assistant Examiner*—Christina Chan
*Attorney, Agent, or Firm*—Alice O. Robertson; Michael C. Sudol

[57] ABSTRACT

Process and compositions for lowering blood pressure in diabetic by employing a cyclopeptide compound is described.

7 Claims, 2 Drawing Sheets

ANTIHYPERTENSIVE THERAPY FOR DIABETICS

The present invention is directed to a method for controlling hypertension. It is particularly directed to controlling hypertension in diabetics.

BACKGROUND OF THE INVENTION

Hypertension is a serious and quite common disease. Probably about twenty percent of the adult population may be affected by hypertension. It is further a major risk factor for the more serious cardiovascular diseases. Thus, control of hypertension is essential and it is most frequently carried out by drug therapy. However, it is known that some side effects are frequently encountered in drug therapy. This is more serious if the patient is suffering from some other disease such as diabetes. Thus, for example, care must be taken with diabetics if hydrazide, hydralazine or thiazide therapy is employed, in order to avoid serious consequences. Moreover, hydrazide therapy has been found to cause diabetes, which has been latent, to become manifest. It is desirable therefore that a drug be found which has a selective action in being positive toward diabetes and which thus may be employed for antihypertensive therapy for diabetic patients.

DESCRIPTION OF THE INVENTION

According to the present invention it has been discovered that elevated blood pressure in diabetes may be normalized by the administration of a composition comprising an antihypertensive amount of a cyclopeptide compound and that this can be accomplished without the side effects normally associated with antihypertensive drugs and which have especially adverse effects on diabetics.

The cyclopeptide compound useful in the present invention are cyclic and bridged cyclic peptides having somatostatin-like activity and often referred to in the literature as somatostatin analogs. Particularly useful compounds are cylic hexapeptides or cyclic octapeptides, or cyclopeptides which contain a cyclic octapeptide or hexapeptide in their structure. These compounds and methods for preparation which may be employed and which are described in U.S. Pat. Nos. 4,310,518; 4,235,886; 4,522,813; 4,358,439; 4,238,481; and 4,585,755; U.S. patent application Ser. No. 748,069, filed June 24, 1985 now U.S. Pat. No. 4,663,435; U.K. patent application, GB No. 2095261A; European patent application No. 187,622; and in papers by W. Bauer et al., in Peptides 1982, edited by K. Blaka and P. Malon, Walter de Gruyter, New York, 1983; J. Pless et al., Scand. J. Gastroenterol 1986, 21 (suppl 119) 54–64; W. Bauer et al., Life Sciences, 31, pp 1133–1140 (1982); J. Rivier, J. Am. Chem-Soc. 96, 2986 (1974); J. Rivier et al., J. Med. Chem. 18, 123 (1975); W. Vale et al., Metabolism, 27, Suppl 1, pp 1391–1401 (1978); are incorporated herein by reference.

The more important groups of these compounds are the cyclic hexapeptides and octapeptides embraced in the following formulas:

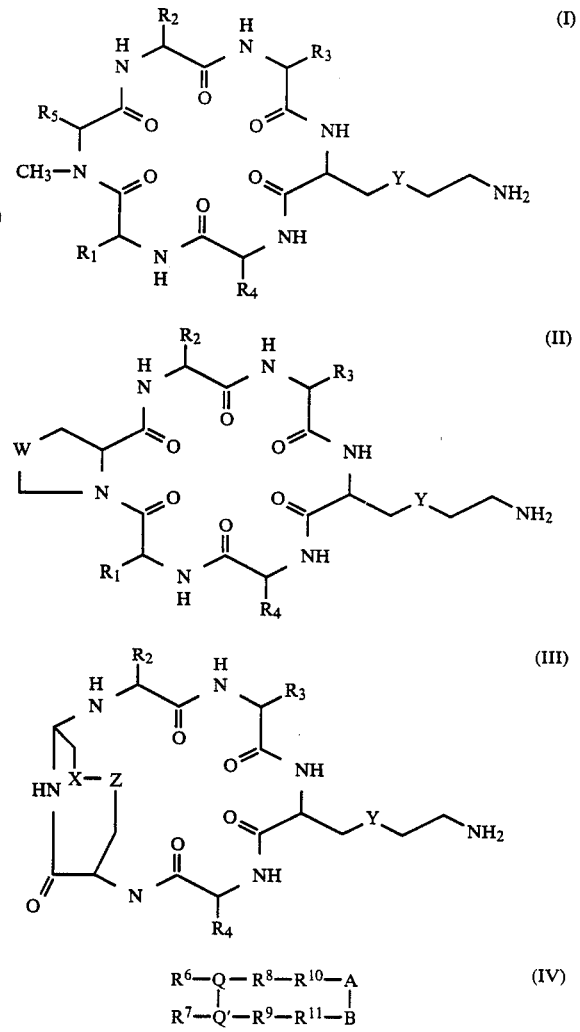

and the pharmaceutically acceptable salts thereof.

In Formulas I, II and III,

W is sulfur or $(CH_2)_n$ wherein n is 0, 1 or 2;

X and Z are sulfur or $CH_2$ provided that at least one of X or Z is sulfur,

Y is $(CH_2)_m$ wherein m is 0, 1 or 2, or sulfur, wherein if it may be in any position along the chain.

$R_1$ and $R_2$ are independently lower alkyl, benzyl, substituted benzyl wherein the substituent may be one or two of lower alkyl, halogen, hydroxy, amino, nitro or lower alkoxy; and lower alkyl substituted with a 5- or 6-membered heterocyclic ring;

$R_3$ is 3 indolylmethyl or substituted 3-indolylmethyl wherein the substituent may be lower alkyl, lower alkoxy or halogen;

$R_4$ is lower alkyl, hydroxy-lower-alkyl, benzyl, carboxy-lower-alkyl, amino-lower-alkyl or substituted benzyl wherein the substituent may be lower alkyl, lower alkoxy, hydroxy, halogen, amino or nitro; and $R_5$ is hydrogen, lower alkyl, benzyl, or substituted benzyl wherein the substituent is lower alkyl, lower alkoxy, hydroxy, halogen, amino or nitro.

In the compound of Formula IV,

A is (D)-Trp

B is Lys

Q is Cys or Asn; and

Q' is Cys, or when Q is Asn and $R^6$ and $R^7$ are absent is Gaba.

$R^6$ is (D)-Phe, $CH_3(CH_2)_8CO(D)Phe$, or is absent;

$R^7$ is Thr or is absent or is $NH_2$, -(D)Ser($NH_2$), (D)Thr($NH_2$), Ser(ol), Phe(ol), (D)-Thr(ol) or Thr(ol).

$R^8$ and $R^9$ *are independently Phe or is absent*;

$R^{10}$ is Phe or Tyr;

$R^{11}$ *Is Val or Thr*;

In the Formulas I, II and III compounds, the term "lower alkyl" represents those alkyl groups either straight or branched chain, which have from 1-5 carbon atoms. Examples of such alkyl groups are methyl, ethyl, propyl, iso-propyl, butyl, sec-butyl, pentyl and the like.

The term "lower alkoxy" represents those alkoxy groups of from 1-5 carbon atoms, in either a straight or branched chain. Examples of such alkoxy groups are methoxy, ethoxy, propoxy, isopropoxy, butoxy, tert-butoxy, pentoxy and the like.

The term "halogen or "halo" represents fluorine, chlorine, bromine and iodine.

The term "5- or 6-membered heterocyclic ring" represents those 5- and 6-membered heterocycles with 1- or 2-hetero atoms selected from oxygen, nitrogen and sulfur. Exemplary of such heterocycles is imidazole, furan, thiazole, pyrazole, pyridine and the like.

In Formula IV, and in subsequent representations of cyclic peptides, the amino acid components of the peptide chain are referred to by shorthand designations conventionally employed in the peptide field.

The designations and meanings are as follows:

| Abbreviation | Amino Acid |
| --- | --- |
| Ala | alanine |
| N—Me—Ala | N—methylalanine |
| Lys | lysine |
| Phe | phenylalanine |
| Trp | tryptophan |
| Thr | threonine |

| Abbreviation | Amino Acid |
| --- | --- |
| Thr(ol) | threoninol |
| Aha | aminoheptanoic acid |
| Tyr | tyrosine |
| Val | valine |
| Abu | α-aminobutyric acid |
| Ser | serine |
| Asn | asparagine |
| Pro | proline |
| Asu | aminosuberic acid |
| Cys | cysteine |
| Gaba | α-aminobutyric acid |

The amino acids components of the peptides have an asymmetric center with possible (D) and (L) configurations. Although all optical isomers are encompassed, most of the peptides are of amino acids the (L) configuration and when the component amino acid is of the (L) configuration, the (L) designation is omitted. When the amino acid component is of the (D) configuration, (D) is inserted before the abbreviation of the amino acid.

The most preferred compounds for the practice of the present invention are those within Formula I and in Formula II. Thus, the most preferred compound from Formula I group may be designated cyclo-(N-MeAla-Tyr-(D)Trp-Lys-Val-Phe) or

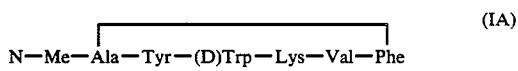
(IA)

and may be represented by the formula

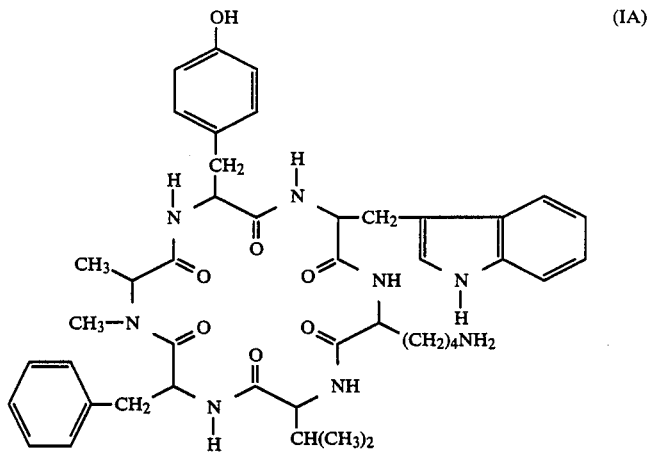
(IA)

Another preferred compound from Formula IV group may be designated

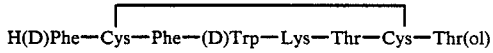

and may be represented by the formula

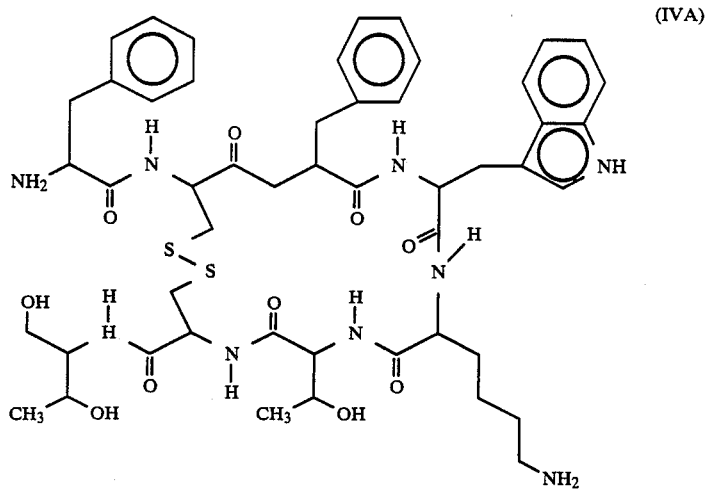

(IVA)

Other especially preferred compounds are:

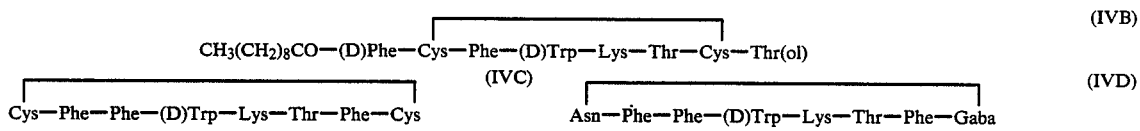

(IVB)

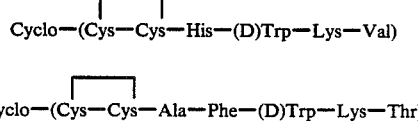

(IVC)  (IVD)

Other suitable compounds include from Formula I:
Cyclo-(N-Me-Ala-Tyr-(D)Trp-Lys-Thr-Phe);
Cyclo-(N-Me-Ala-Phe-(D)Trp-Lys-Thr-Phe);
Cyclo-(N-Me-Ala-Phe-(L)Trp-Lys-Thr-Phe);
Cyclo-(N-Me-Ala-Phe-(D)Trp-Lys-Thr-p-Cl-Phe);
Cyclo-(N-Me-Ala-Phe-(D)5-F-Thr-Lys-Thr-Phe);
Cyclo-(N-Me-Ala-Phe-(L)5-F-Thr-Lys-Thr-Phe);
Cyclo-(N-Me-Ala-Phe-(D)Trp-Lys-Ser-Phe);
Cyclo-(N-Me-Ala-Tyr-(D)Trp-Lys-Val-Trp);
Cyclo-(N-Me-Ala-Tyr-(L)Trp-Lys-Val-Phe);
Cyclo-(Ser-Ala-N-Me-Phe-His-(D)-Trp-Lys).
form Formula II:
Cyclo-(Pro-Tyr-(D)Trp-Lys-Thr-Phe)
Cyclo-(Pro-Phe-(D)Trp-Lys-Thr-Phe)
Cyclo-(Pro-Phe-(L)Trp-Lys-Thr-Phe)
Cyclo-(Pro-Phe-(D)Trp-Lys-Thr-p-Cl-Phe)
Cyclo-(Pro-Phe-(D)5-F-Trp-Lys-Thr-Phe)
Cyclo-(Pro-Phe-(L)5-F-Trp-Lys-Thr-Phe)
Cyclo-(Pro-Phe-(D)Trp-Lys-Ser-Phe)
from formula III:

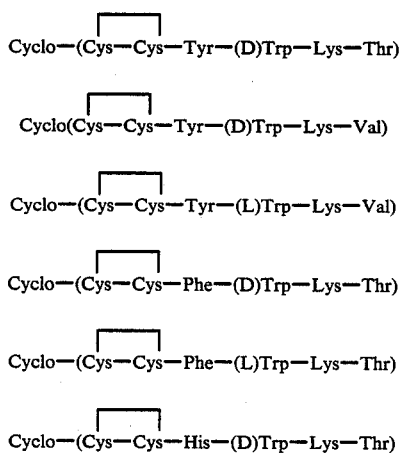

The cyclopeptides may be employed in the form of pharmaceutically acceptable salts, particularly those cyclopeptides in which lysine is a component. Suitable acid addition salts include acetates, hydrochlorides, hydrobromides, maleates, lactates, citrates, bicarbonates and the like.

The cyclopeptide compound may be prepared by first forming linear peptides by methods known in the art of peptide chemistry or by obvious equivalents thereof, then removing a protecting group and cyclizing. In one method, the linear peptide is prepared by solid phase sequential synthesis on a chloromethylated resin. The amino acid selected to be the C-terminal amino acid is converted to its amino protected derivative and bound covalently to the resin support. Then the protecting group is removed and the amino protected derivative of the next amino acid in sequence is added along with a coupling agent such as dicyclohexylcarbodiimide. Deprotection and addition of successive amino acids is performed until the desired linear peptide is formed.

The linear peptide may be removed from the resin by any knwon method. Conveniently, it is removed by cleaving with hydrazine, thereby froming the peptide hydrazide which may then be cyclized via the azide to the desired cyclic peptide using a reagent furnishing nitrous acid in situ.

The solid phase method is more fully described in J. Rivier, J. Am-Chem. Sac. 96, 2986(1974), in U.S. Pat. No. 4,310,518 and in the other references previously cited and incorporated by reference. The cyclization also may be carried out as described in U.S. Pat. No. 4,358,439.

When the cyclopeptide is joined by a disulfide group, ring closure of the appropriate linear polypeptide may be carried out by treating a solution of the open chain polypeptide in trifluoracetic acid with boron tris-fluoroacetate as more fully described in GB No. 2,095,261A, teachings of which are incorporated by reference.

The cyclopeptide compounds have been found to alleviate hypertension uniquely in diabetic animals. It has further been found that there is no increase in weight or in serum glucose leve. The cyclopeptide compound appears to have this beneficial therapeutic property without undesirable side effects. The desirable therapeutic effect of the cyclopeptide compounds on the blood pressure may be seen in the following representative operation with cyclo-(NMeAla-Tyr-(D)Trp-Lys-Val-Phe), compound IA.

In the determination, the following groups of rats were employed, each group consisting of ten rats.
Group 1 Normal rats
Group 2 Diabetic rats
Group 3 Diabetic rats treated with cyclopeptide compound
Group 4 Spontaneously hypertensive (SH) rats
Group 5 Spontaneously hypertensive rats treated with cyclopeptide compound Normal rats were commercially available laboratory rats identified as CD rats.

Diabetic rats were CD rats in which diabetes was induced by the injection of streptozotocin into the femoral vein at a dose of 60 mg/kg. Hyperglycemia was confirmed by measuring glucose levels in blood obtained by orbital bleeding. (A standard medical technique for obtaining blood form the orbital sinus is described in "Laboratory Animal Medicine" edited by J. G. Fox et al., Academic Press, Inc., Orlando, Fla., 1984.)

SH rats were commercially available spontaneously hypertensive rats.

Dosing was initiated with cyclopeptide compound four days after injection of streptozotocin to induce diabetes in the diabetic rats. Dosing was carried out by administering the cyclopeptide compound in the drinking water at a dose of 50 μg/rat/day.

The rats were housed two to a box and fed standard rat food and water ad libitum. Blood pressure was measured indirectly with a photoelectric system with a tail cuff containing a built in sensor (Harvard Biosciences, Cambridge, MA). The instrument was calibrated on each day of use with a sphygmomanometer. Six to eight recordings were made for each rat.

At the beginning of the experiment, the mean weights of the CD rats were 160 grams and the SH rats were 220 grams. The body weights after 38 days may be seen in Table 1. The serum glucose level, measured after 27 days of treatment also may be seen in Table 1. It can be seen that treatment with the cyclopeptide compound had no significant effect either on body weight or serum glucose level of either the diabetic rat or the spontaneously hypertensive rat.

Blood pressure measurements were initated 8 days following injection of streptozotocin (4 days after start of treatment). The results are shown in FIG. 1.

FIG. 1 is a graph in which the blood pressures of normal, diabetic and treated diabetic rats are plotted against a period of time in days. (Each point is the mean of 7 to 10 rats±standard deviation.)

TABLE 1

| Rats | Body Weight (gms) (after 38 days) | Serum Glucose (mg %) (after 27 days) |
|---|---|---|
| Normal CD | 400 ± 40 | 102 ± 14 |
| Diabetic CD | 261 ± 43 | 368 ± 22 |
| Diabetic CD + Compound IA | 281 ± 63 | 352 ± 52 |
| SH | 286 ± 13 | 80 ± 12 (P = <0.005)* |
| SH + Compound IA | 285 ± 17 | 90 ± 10 (P = <0.05)* |

All values are the mean ± std. dev.
*Relative to normal CD

At the time of initial determination, all diabetic rats were found to exhibit elevated blood pressure when compared with normal rats. The first point shows that the blood pressure of diabetic rats was 15% above that of the normal rats (P= <0.025).

Untreated diabetic rats exhibited a mean systolic blood pressure which was 11 to 23 percent higher than that of normal rats. All these elevations were statisically significant with the exception of the second determination (+10%, P= <0.1).

In the treated diabetic rats, the blood pressure was reduced by 14 percent (P= <0.05) after 17 days of treatment. The dose of the drug was doubled to 100 micrograms/rat/day (μg/rat/day) on the 21st day of treatment. Readings taken on the 33rd and 38th day of treatment showed reductions in blood pressure of 18 percent and 21 percent, respectively. These results are highly significant (P= <0.005 and <0.001, respectively).

Figure 2:
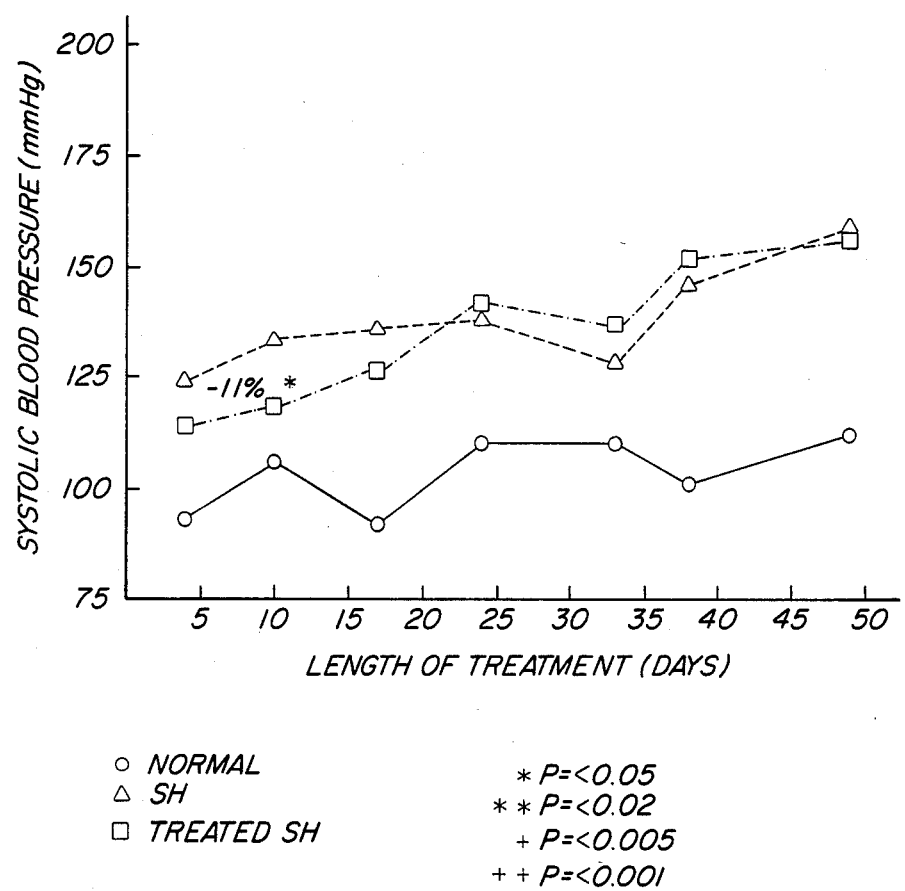

The blood pressure measurements of treated and untreated spontaneously hypertensive rats compared with normal rats may be seen in FIG. 2.

FIG. 2 is a graph in which the systolic blood pressure of normal, spontaneously hypertensive and treated spontaneously hypertensive rats are plotted against a period of time in days. Readings taken on the 10th day of treatment showed a reduction of 11 percent (P= <0.02). Thereafter, blood pressure rose and no further inhibition was evident even after increasing the dose to 200 μg/rat/day on the 40th day of treatment.

The results seen in Table 1 and FIGS. 1 and 2 show that the cyclopeptide Compound IA possesses beneficial antihypertensive properties which may be utilized in the methods and compositions of the present invention.

The process of the present invention, namely, a method for treating hypertension or alleviating high blood pressure, comprises administering to diabetic subjects in need of treatment, a therapeutically effective antihypertensive amount of a cyclopeptide compound. The active agent may be administered in amounts hereinafter set forth.

The amount of the cyclopeptide compound to be administered to diabetic hypertensive patients is generally in the range of 0.14 to 14 micrograms per kilogram of body weight. When administered subcutaneously, the dosing should be about 10–1,000 micrograms/day. When administered intraveneously, the dosing should be about 0.1 to 10.0 micrograms per hour. It is to be understood that the specific dose level for any particular diabetic patient may vary on a variety of factors such as age, body weight, sex, time of administration, general health and severity of disease.

The cyclopeptide compounds may be administered in liquid compositions suitable for parenteral application or may be administered transdermally. They are preferably administered subcutaneously in an acceptable unit dosage form.

For parenteral administration, the carrier will usually comprise sterile water, at least in part, although other ingredients, for example, to aid solubility, may be included. Injectable solutions, for example, may be prepared in which the carrier comprises physiological saline solution or may be injectable suspensions in appropriate aqueous carriers, with solubilizing and/or suspending agents, preservatives and the like. Agents suitable for aqueous injectable compositions in addition to physiological solution such as saline include buffering agents such as citrates, acetates and phosphates, polysorbate 80, sodium carboxymethyl cellulose, preservatives such as methyl paraban and propyl paraban, antimicrobial agents such as thimerosal, benzalkonium chloride, antioxidant such as sodium bisulfite, chelating agents such as sodium salt of ethylenediaminetetraacetic acid; watermiscible vehicles such as ethyl alcohol and nonmiscible vehicles such as ethyl oleate and isopropyl myristate.

The following formulations are representative for an injectable composition but is not to be construed as limiting.

The formulation provides 1 liter of a parenteral solution comprising 1 milligram of cyclo-(NMeAla-Tyr-(D)Trp-Lys-Val-Phe) (Compound IA) as the cyclopeptide compound as active ingredient per milliliter:

| Compound IA | 1.0 |
| Polysorbate 80 | 2.0 |
| Sodium chloride | 9.0 |
| Sodium carboxymethyl cellulose | 9.0 |
| Methyl paraban | 1.8 |
| Propylparaban | 0.2 |
| Water q.s. ad 1 liter | |

Formulation II

The formulation provides 1 liter of a parenteral solution comprising 1 milligram of (Compound IVA)

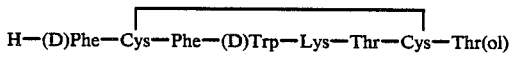
H—(D)Phe—Cys—Phe—(D)Trp—Lys—Thr—Cys—Thr(ol)

as the cyclopeptide compound as active ingredient per milliliter.

| Compound IVA | 1.0 |
| Polysorbate 80 | 2.0 |
| Sodium chloride | 9.0 |
| Sodium carboxymethyl cellulose | 9.0 |
| Methyl paraban | 1.8 |
| Propylparaban | 0.2 |
| Water q.s. ad 1 liter | |

What is claimed is:

1. A method for reducing blood pressure in diabetic patients comprising administering to a diabetic suffering from elevated blood pressure, an antihypertensive amount of a cyclopeptide compound represented by the formula:

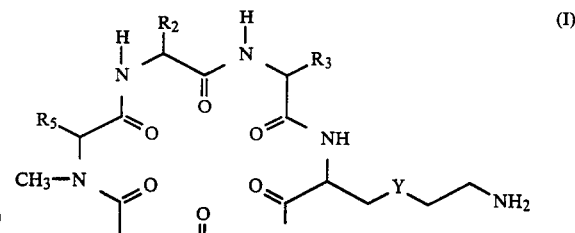

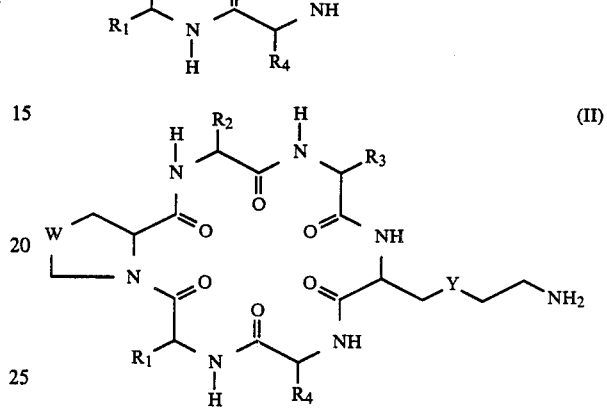

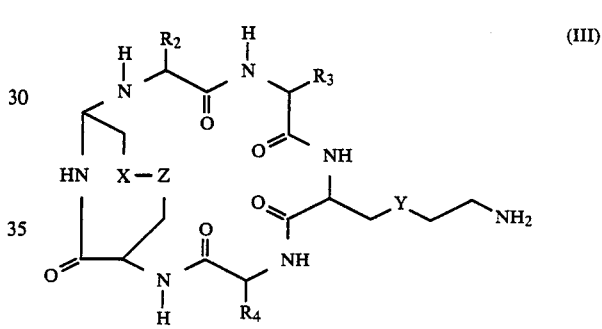

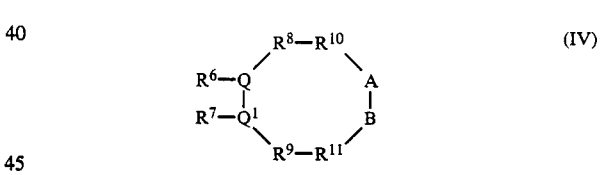

and the pharmaceutically acceptable salts thereof, wherein in Formulas I, II and III Y is $(CH_2)_m$ wherein m is 0, 1 or 2, or sulfur W is $(CH_2)_n$ wherein n is 0, 1 or 2, or sulfur;

X and Z are independently sulfur or $CH_2$ provided that at least one of X or Z is sulfur $R_1$ and $R_2$ are independently lower alkyl, benzyl, substituted benzyl wherein the substituent may be one or two of lower alkyl, halogen, hydroxy, amino, nitro or lower alkoxy; and lower alkyl substituted with a 5- or 6-membered heterocyclic ring with 1 or 2 hetero atoms selected from oxygen, nitrogen, and sulfur;

$R_3$ is 3-indolylmethyl or substituted 3-indolylmethyl wherein the substituent may be lower alkyl, lower alkoxy or halogen;

$R_4$ is lower alkyl, hydroxy-lower-alkyl, benzyl, carboxy-lower-alkyl, amino-lower-alkyl or substituted benzyl wherein the substituent may be lower alkyl, lower alkoxy, hydroxy, halogen, amino or nitro; and $R_5$ is hydrogen, lower alkyl, benzyl, or substituted benzyl wherein the substituent is lower alkyl, lower alkoxy, hydroxy, halogen, amino or nitro;

in Formula IV

A is (D)-Trp

B is Lys

Q is Cys or Asn; and $Q^1$ is Cys or when Q is Asn and $R^6$ and $R^7$ are absent is Gaba $R^6$ is (D)-Phe, $CH_3(CH_2)_8CO(D)Phe$, or is absent;

$R^7$ is Thr or is absent or is $NH_2$, (D)Ser($NH_2$), (D)Thr($NH_2$), Ser(ol), Phe(ol), (D)Thr(ol), or Thr(ol);

$R^8$ and $R^9$ are independently Phe or is absent;

$R^{10}$ is Phe or Thyr; and $R^{11}$ is Val or Thr;

wherein

Trp is a residue of tryptophan

Lys is a residue of lysine

Cys is a residue of cysteine

Asn is a residue of asparagine

Gaba is a residue of α-aminobutyric acid

Phe is a residue of phenylalanine

Thr is a residue of threonine

Thr(ol) is a residue of threoninol

Ser is a residue of serine

Tyr is a residue of tyrosine

Val is a residue of valine and (ol) and ($NH_2$) refer to the alcohol or amine corresponding to the amino acid.

2. A method according to claim 1 wherein the cyclopeptide compound is one which is designated cyclo-(N-Me-Ala-Tyr-(D)Trp-Lys-Val-Phe) and is represented by the formula:

3. A method according to claim 1 wherein the cyclopeptide compound is

H(D)Phe—Cys—Phe—(D)Trp—Lys—Thr—Cys—Thr(ol)

4. A method according to claim 1 wherein the cylcopeptide compound is administered in an amount of from about 0.14 to 14 micrograms per kilogram of body weight.

5. A method according to claim 1 wherein the cyclopeptide compound is administered subcutaneously in an amount of from about 10 to 1,000 micrograms/day.

6. A method according to claim 1 wherein the cyclopeptide is administered intravenously at a rate of from about 0.1 to 10.0 micrograms/hour.

7. A method for reducing blood pressure in diabetic patients comprising administering to a diabetic suffering from elevated blood pressure, an antihypertensive amount of a cyclopeptide compound represented by the formula:

and pharmaceutically acceptable salts thereof wherein

Y is $(CH_2)_m$ wherein m is 0, 1 or 2, or sulfur $R_1$ and $R_2$ are independently lower alkyl benzyl, substituted benzyl wherein the substituent may be one or two of lower alkyl, halogen, hydroxy, amino, nitro or lower alkoxy; and lower alkyl substituted with a 5- or 6-membered heterocyclic ring with 1 or 2 hetero atoms selected from oxygen, nitrogen, and sulfur;

$R_3$ is 3-indolylmethyl or substituted 3-indolylmethyl wherein the substituent may be lower alkyl, lower alkoxy or halogen;

$R_4$ is lower alkyl, hydroxy-lower-alkyl, benzyl, carboxy-lower-alkyl, amino-lower-alkyl or substituted benzyl wherein the substituent may be lower alkyl, lower alkoxy, hydroxy, halogen, amino or nitro; and $R_5$ is hydrogen, lower alkyl, benzyl, or substituted benzyl wherein the substituent is lower alkyl, lower alkoxy, hydroxy, halogen, amino or nitro.

* * * * *